US011035792B2

(12) United States Patent
Zhao et al.

(10) Patent No.: US 11,035,792 B2
(45) Date of Patent: Jun. 15, 2021

(54) NANOHOLE ARRAY BASED SENSORS WITH VARIOUS COATING AND TEMPERATURE CONTROL

(71) Applicant: The George Washington University, Washington, DC (US)

(72) Inventors: Yangyang Zhao, Rockville, MD (US); Mona Zaghloul, Bethesda, MD (US); Stephen Semancik, Gaithersburg, MD (US); Kurt D. Benkstein, Poolesville, MD (US)

(73) Assignees: The George Washington University, Washington, DC (US); GOVERNMENT OF THE UNITED STATES OF AMERICA, AS REPRESENTED BY THE SECRETARY OF COMMERCE, NATIONAL INSTITUTE OF STANDARDS AND TECHNOLOGY, Gaithersburg, MD (US)

( * ) Notice: Subject to any disclaimer, the term of this patent is extended or adjusted under 35 U.S.C. 154(b) by 0 days.

(21) Appl. No.: 16/294,686

(22) Filed: Mar. 6, 2019

(65) Prior Publication Data
US 2019/0277762 A1 Sep. 12, 2019

Related U.S. Application Data

(60) Provisional application No. 62/639,328, filed on Mar. 6, 2018.

(51) Int. Cl.
*G01N 21/552* (2014.01)
*G01N 33/543* (2006.01)
*G01N 21/03* (2006.01)
*G01N 21/17* (2006.01)

(52) U.S. Cl.
CPC ....... *G01N 21/554* (2013.01); *G01N 21/0332* (2013.01); *G01N 21/1717* (2013.01); *G01N 33/54366* (2013.01); *G01N 2021/1731* (2013.01)

(58) Field of Classification Search
CPC ............ G01N 21/554; G01N 21/0332; G01N 21/1717; G01N 33/54366; G01N 2021/1731
See application file for complete search history.

(56) References Cited

U.S. PATENT DOCUMENTS

| | | | |
|---|---|---|---|
| 4,948,496 A * | 8/1990 | Chand | G01N 27/404 204/408 |
| 5,345,213 A | 9/1994 | Semancik et al. | |
| 10,466,190 B1 * | 11/2019 | Ancona | G01N 1/405 |
| 2006/0034729 A1 * | 2/2006 | Poponin | G02B 5/204 422/82.05 |

(Continued)

OTHER PUBLICATIONS

Kreno, et al., Metal-Organic Framework Materials as Chemical Sensors, Chem. Rev. 2012, 112:1105-1125.

(Continued)

*Primary Examiner* — Jamil Ahmed
(74) *Attorney, Agent, or Firm* — Blank Rome LLP

(57) ABSTRACT

A nanohole array (NHA)-based plasmonic sensor (e.g., gas/condensed phase sensor), their preparation, and their use to detect and analyze samples, especially mixtures of chemicals/bio-chemicals.

44 Claims, 15 Drawing Sheets

(56) References Cited

U.S. PATENT DOCUMENTS

| | | | | |
|---|---|---|---|---|
| 2007/0251822 A1* | 11/2007 | Hoagland | .............. | B82Y 30/00 |
| | | | | 204/424 |
| 2009/0221447 A1* | 9/2009 | Mur | .................. | G11C 13/0009 |
| | | | | 506/17 |
| 2013/0065777 A1* | 3/2013 | Altug | .................. | G01N 33/553 |
| | | | | 506/9 |
| 2013/0295325 A1* | 11/2013 | Shah | ....................... | B44C 1/227 |
| | | | | 428/138 |
| 2014/0256593 A1* | 9/2014 | Szmacinski | ...... | G01N 33/54373 |
| | | | | 506/9 |
| 2017/0038326 A1* | 2/2017 | Motayed | ............ | G01N 33/0054 |

OTHER PUBLICATIONS

Kreno, et al., Metal-Organic Framework Thin Film for Enhanced Localized Surface Plasmon Resonance Gas Sensing, Anal. Chem., 2010, 82:8042-8046.

Kreno, et al., SERS of molecules that do not adsorb on Ag surfaces: a metal-organic framework-based functionalization strategy†, Analyst, 2014, 139:4073-4080.

* cited by examiner

FIGURE 3
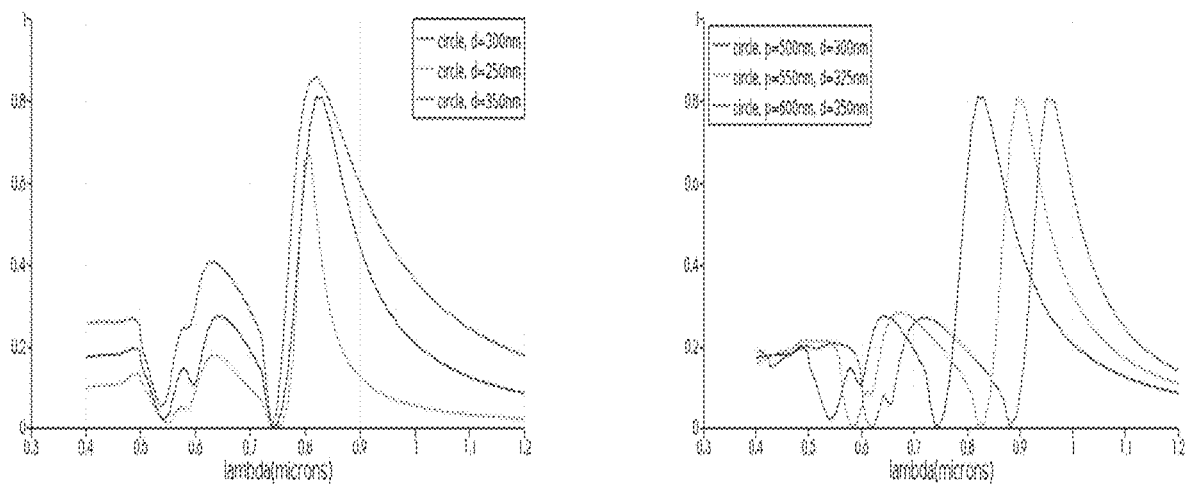
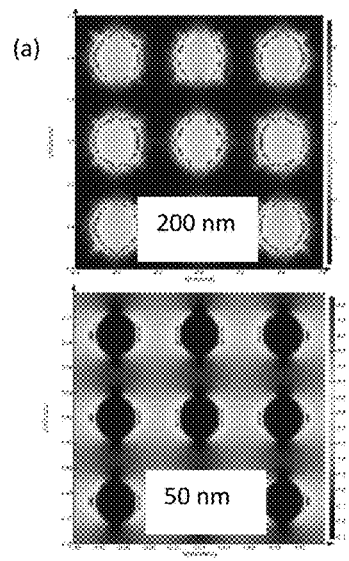
FIGURE 4a
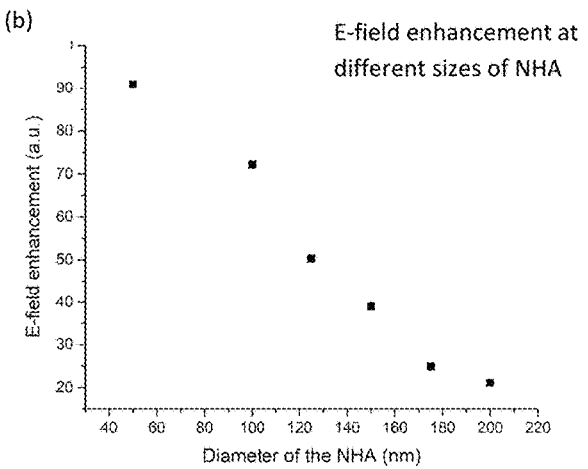
FIGURE 4b

NANOHOLE ARRAY BASED SENSORS WITH VARIOUS COATING AND TEMPERATURE CONTROL

The present application claims the benefit of U.S. Provisional Application No. 62/639,328 filed Mar. 6, 2018, which is hereby incorporated by reference in its entirety.

FIELD OF THE INVENTION

The present invention relates to nanohole array (NHA) based plasmonic sensors (e.g., gas/condensed phase sensors), their preparation, and their use in the detection and analysis of samples (including mixtures of chemicals and/or bio-chemicals).

BACKGROUND OF THE INVENTION

Technological advancement, cost reduction and miniaturization are key factors that often determine the commercial adaptability and sustainability of a device. Plasmonic platforms are attractive for developing different kinds of miniaturized devices for modern and advanced applications, which include, e.g., nanoantennae, waveguides, modulators, and sensors. See. e.g., Liu et al., *Nature Materials*, 10, 631, 2011, Maier et al., *Nature Materials*, 2, 229, 2003, Ma et al., *IEEE Journal of Selected Topics in Quantum Electronics*, 23, 81-88, 2017, Nielsen et al., *Science*, 358, 1179-1181, 2017, and Belushkin et al., *ACS Nano*, 12, 4453-4461, 2018.

Plasmonic platforms enable localized surface plasmon resonance (LSPR) in the presence of electromagnetic radiation and produce strong resonating signals. See, e.g., Maier et al., *Nature Materials*, 2, 229, 2003, Willets et al., *Ann. Rev. Phys. Chem.*, 58, 267-297, 2007 and Genet et al., *Nature*, 445, 39, 2007.

In a typical plasmonic sensor, changes in the refractive index of the surrounding dielectric medium due to the presence of target analytes alter the nature (intensity, wavelength) of the resonating signal. In recent years, considerable research efforts have been undertaken towards developing miniaturized plasmonic sensors for the detection of a wide variety of target analytes, such as biomolecules and gases. See, e.g., Willets et al., *Ann. Rev. Phys. Chem.*, 58, 267-297, 2007, Stewart et al., *Chem. Rev.*, 108, 494-521, 2008, Li et al., *Analyst*, 140, 386-406, 2015, and Anker et al., *Nanoscience and Technology: A Collection of Reviews from Nature Journals*, World Scientific, 308-319, 2010.

Typically, plasmonic sensors are most attractive for the detection of biomolecules in condensed phase applications. See, e.g., Willets et al., *Ann. Rev. Phys. Chem.*, 58, 267-297, 2007, Stewart et al., *Chem. Rev.*, 108, 494-521, 2008, Mehta et al., *Scientific Reports*, 6, 21287, 2016, and Zhao et al., *IEEE Photonics Conference* (IPC), 1-2, 2018.

However, poor adsorption of gases over noble metal (such as gold and silver) based plasmonic platforms possibly restricts development of high performance plasmonic gas sensors, since the refractive index of the medium surrounding the plasmonic platform does not change sufficiently to produce a distinguishable signal change under the exposure of very low concentrations (sub µmol/mol and nmol/mol) of a gas-phase target analyte. See, e.g., Belushkin et al., *ACS Nano*, 12, 4453-4461, 2018, Stewart et al., *Chem. Rev.*, 108, 494-521, 2008, Zhao et al., *IEEE Photonics Conference* (IPC), 1-2, 2018, and Tittl et al., *Nanophotonics*, 3, 157-180, 2014.

In developing a miniaturized, room-temperature operable sensor on a plasmonic platform, a key challenge is to enhance the response strength of the sensor towards target gases. One approach to address the challenge is to improve the refractive index change by modifying the surface pattern of the platform. Additionally, the modification of the patterned plasmonic platforms with porous receptors (e.g., metal organic frameworks (MOFs)) may facilitate the adsorption of gaseous analyte leading to a stronger plasmonic response. See. e.g., Kreno et al., *Chem. Rev.*, 112, 1105-1125, 2011, and Achmann et al., *Sensors*, 9, 1574-1589, 2009.

MOFs are an attractive class of materials for the adsorption of gases due to their large internal surface area and small-molecule scale pores with stable crystalline structure. See, e.g., Li et al., *Chem. Soc. Rev.*, 38, 1477-1504, 2009, and Adatoz et al., *Separation and Purification Technology*, 152, 207-237, 2015.

However, detecting low concentration (e.g., nmol/mol concentrations) of other gaseous analytes with plasmonic sensors is still demanded for various applications, including, for example:

i) food safety (see, e.g., Carotta et al., *Sensors and Actuators B: Chemical*, 58, 310-317, 1999, and Tsujita et al., *Sensors and Actuators B: Chemical*, 110, 304-311, 2005), ii) environmental monitoring (see, e.g., Kuswandi et al., *Sensing and Instrumentation for Food Quality and Safety*, 5, 137-146, 2011, Khot et al., *Sensors and Actuators B: Chemical*, 153, 1-10, 2011, and Fenske et al., *Journal of the Air & Waste Management Association*, 49, 594-598, 1999), and iii) disease diagnostics (see, e.g., Lourenço et al., *Metabolites*, 4, 465-498, 2014. Peng et al., *Br. J. Cancer*, 103, 542, 2010, Phillips et al., *J. Chromatography B: Biomedical Sciences and Applications*, 729, 75-88, 1999, and Blaikie et al., *J. Breath Res.*, 8, 046010, 2014).

Studies have shown that, for example, the concentration of acetone in the exhaled breath of diabetes patients exceeds 1.8 µmol/mol (ppm), which is two to six-fold higher than that (0.3-0.9 µmol/mol) of people without diabetes. See, e.g., Lourenço et al., *Metabolites*, 4, 465-498, 2014, Liu et al., *NPG Asia Materials*, 1, 2018, and Peled et al., *J. Thoracic Onc.*, 7, 1528-1533, 2012.

There is therefore a need for new sensors that can be used in the detection and analysis of low concentration (e.g., nmol/mol) gas samples.

SUMMARY OF THE INVENTION

The present invention relates to nanohole array (NHA) based plasmonic sensors (e.g., gas/condensed phase sensors), their preparation, and their use in the detection and analysis of samples (including mixtures of chemicals and/or bio-chemicals).

The sensors of the present invention exhibit one or more of the following benefits, which are described in more detail herein:

(i) they can detect different samples with low limits of detection, such as detection of gases at part-per-billion (e.g., 100 nmol/mol) levels;

ii) they can be operated at different temperatures, allowing for enhanced discrimination between samples and optimized analysis of different components within a sample;

iii) they can be coated with a combination of materials, thereby allowing for the measurement of different gas analytes; and iv) they can be adapted for use with everyday optical apparatus, such as cell phone cameras, thereby providing a lower cost alternative to the use of costly spectrometers in such analysis.

Accordingly, in one aspect, the present invention relates to a nanohole array based plasmonic sensor (e.g., a gas sensor) comprising:

i) a substrate (e.g., an etchable substrate, such as a Si substrate) at least partially covered (e.g., at least partially covered on both sides) with a deposit (such as a $Si_3N_4$ deposit);

ii) a plasmonic layer on the deposit (e.g., a gold layer); and iii) one or more functional layers (e.g., a porous absorptive material or capture affinity layer, such as a metal organic framework) on the plasmonic layer;

wherein the sensor comprises a plurality of nanoholes.

In one embodiment (e.g., for a gas-phase application), the substrate is silicon. In another embodiment, (e.g., for a condensed/liquid phase application), the substrate is selected from glass, silica, fused-silica, quartz, sapphire, and any combination thereof. In a preferred embodiment the substrate is silicon.

In one embodiment, the substrate is at least partially covered (e.g., at least partially covered on both sides) with a deposit comprising $Si_3N_4$, $SiO_2$, or any combination thereof. In a preferred embodiment, the substrate is at least partially covered with a deposit comprising $Si_3N_4$.

In one embodiment, the deposit has a thickness of between about 20 nm and about 600 nm, such as between about 20 nm and about 150 nm or between about 75 nm and about 150 nm. In a preferred embodiment, the deposit has a thickness of about 100 nm.

In one embodiment, the substrate is fully covered (e.g., fully covered on both sides) with the deposit.

In one embodiment, the plasmonic layer comprises gold, silver, copper, aluminum, platinum, or any combination thereof. In another embodiment, the plasmonic layer comprises gold, silver, or a combination thereof. In a preferred embodiment the plasmonic layer comprises gold.

In one embodiment, the plasmonic layer has a thickness of between about 50 nm and about 300 nm, such as between about 50 nm and about 100 nm. In a preferred embodiment, the plasmonic layer has a thickness of about 80 nm.

In one embodiment, the functional layer comprises a porous absorptive material or capture affinity layer, such as a metal organic framework (MOF), DNA, a protein, an aptamer, or any combination thereof. In one embodiment, the functional layer comprises copper 1,3,5 benzenetricarboxylate (Cu-BTC), iron 1,3,5 benzenetricarboxylate (Fe-BTC), DNA, a protein, an aptamer, or any combination thereof. In one embodiment, the functional layer comprises Cu-BTC, Fe-BTC, or a combination thereof. In one embodiment, the functional layer coating comprises Cu-BTC.

In one embodiment, the one or more functional layers (such as one or more MOF layers) have a thickness of between about 5 nm and about 20 nm, such as between about 10 nm and about 20 nm, or between about 12 nm and about 18 nm. In a preferred embodiment, the one or more functional layers have a thickness of about 15 nm.

In one embodiment, any of the sensors described herein comprise between 1 and about 20 layers of the functional layer (e.g., MOF), such as with between about 5 and about 20 or between about 10 and about 20 layers of the functional layer (e.g., MOF). For example, any of the sensors described herein comprise 1, 2, 3, 4, 5, 6, 7, 8, 9, 10 11, 12, 13, 14, 15, 16, 17 18, 19 or 20 layers of the functional layer (e.g., MOF). In a preferred embodiment, the sensors described herein comprise between about 13 and about 17 layers, such as, in a more preferred embodiment, about 15 layers of the functional layer (e.g., MOF).

In one embodiment, arrays of sensors can be coated with different functional layer material, such as different MOFs, in order to measure different gas analytes. This can help make the device a general-purpose gas sensor.

For example, in one embodiment, the functional layer (such as an MOF) adsorbs chemicals/biochemicals from gas-phase or condensed phase samples thereby allowing detection of target species.

In another embodiment, the functional coating comprises a biological coating. The biological coating attracts and binds biomolecules of interest in the vicinity of the nanoholes. In this embodiment, the biological coating can be a biological layer comprising, e.g., DNA, a protein, an aptamer, or other biomaterial, including combinations thereof. The biological layer is sufficiently thin and of the appropriate density to allow interaction with the biomolecule.

In one embodiment, the nanoarray sensor comprises circular, square or bowtie shaped nanoholes, or any combination thereof. In a preferred embodiment, the nanoarray sensor comprises circular nanoholes.

In one embodiment, the nanoholes have a diameter ranging between about 10 nm and about 500 nm, such as between about 50 nm and about 350 nm, between about 100 nm and about 350 nm, between about 150 nm and about 350 nm, or between about 200 nm and about 350 nm. In one embodiment, the nanoholes have a diameter of about 25 nm, about 50 nm, about 75 nm, about 100 nm, about 125 nm, about 150 nm, about 175 nm, about 200 nm, about 225 nm, about 250 nm, about 275 nm, about 300 nm, about 325 nm, or about 350 nm. In one embodiment, the nanoholes have a diameter of about 50 nm. In another embodiment, the nanoholes have a diameter of about 200 nm.

In one embodiment, the period of the nanoholes is between about 100 nm and about 1000 nm, such as between about 300 nm and about 600 nm or between about 400 nm and about 500 nm. In one embodiment, the period of the nanoholes is about 400 nm. In another embodiment, the period of the nanoholes is about 500 nm.

In another embodiment, the nanoholes are further coated with nanoparticles, e.g., in order to further enhance the electric field. In one embodiment, the nanoparticles comprise, e.g., gold, silver, copper, titanium, platinum, and any combination thereof. In one embodiment, the nanoparticles range in size between about 5 nm and about 30 nm.

In one embodiment, a nanosensor according to any of the embodiments described herein further comprises a heater, such as an integrated heater. The integrated heater may be used to control the temperature of the functional (e.g., MOF) layer.

In one embodiment, the integrated heater is a Pt based heater. In certain embodiments, the integrated heater is square or circular. In one embodiment, the integrated heater surrounds the nanohole array structure, thereby avoiding disruption of the optical performance of the nanohole array. The addition of the heater is realized in a manner that maintains the overall planar structure of the sensing platform.

In one embodiment, the integrated heater is applied before application of the plasmonic layer.

In one embodiment, a non-conductive (insulating) layer (such as an oxide layer, e.g., a silicon oxide layer) is present between the integrated heater, substrate and the plasmonic layer.

In one embodiment, any of the sensors described herein operate at controlled temperatures. For fixed temperature operation, the sensor can operate at (i.e., taking an optical measurement while the sensor is at the desired temperature) about room temperature, at about 30° C., at about 35° C., at about 40° C. or at about 45° C. The sensors can also be operated to measure signals over a range of temperatures, for example as the sensor is at varied temperatures between room temperature (such as at about 20-25° C.) and about 30° C., between room temperature and about 35° C., between room temperature and about 40° C. and between room temperature and about 45° C. Measurements can be taken continuously or at desired steps as the temperature varies. Temperatures above room temperature can be provided by operation of the heater.

In one embodiment, where the functional layer is able to withstand high temperatures in the adsorption (and desorption and/or reaction) process(es), the sensors described herein can be operated at fixed temperatures or with temperature variation, ranging from about room temperature to about 100° C., from room temperature to about 250° C., from room temperature to about 500° C., or even from room temperature to about 750° C. Extended temperature ranges are accessible owing to the ultra-thin and low thermal-mass of the active nanohole array-sensing area located at the membrane. Temperatures above room temperature can be provided by operation of the heater.

In another aspect, the present invention relates to a method of making a nanosensor according to any of the embodiments described herein.

In one embodiment, the method comprises:

(i) depositing a covering (such as $Si_3N_4$) on a substrate (e.g., an etchable substrate, such as a Si substrate);

(ii) patterning a nanohole array on the covered substrate;

(iii) depositing an insulating layer on the substrate while keeping the nanohole array area open;

(iv) patterning a heater (such as a Pt heater) on the covered substrate;

(v) patterning a membrane window on the backside of the coating on the coated substrate;

(vi) etching the substrate to create the membrane, (vii) depositing a plasmonic layer (such as a gold layer) on top of the sample, wherein the plasmonic layer is deposited at the central area with respect to the heater; and (viii) coating the plasmonic layer with one or more functional layers (e.g., one or more MOF layers).

In one embodiment, step (i) is conducted by low-pressure chemical vapor deposition (LPCVD).

In one embodiment, step (ii) is conducted using a deep UV stepper and reactive ion etching (RIE).

In another embodiment, step (ii) is conducted using E-beam lithography and RIE etching.

In one embodiment, step (iii) is conducted using a mask aligner and E-beam evaporator.

In one embodiment, step (iv) is conducted using a mask aligner and E-beam evaporator.

In one embodiment, step (v) is conducted using a mask aligner and RIE etching.

In one embodiment, step (vi) is conducted using KOH.

In one embodiment, step (vii) is conducted using an E-beam evaporator.

In another aspect, the present invention relates to a method of detecting/analyzing one or more gases present in a gas sample or analyzing a condensed phase sample, the method comprising (i) providing a nanohole sensor according to any of the embodiments described herein;

(ii) contacting the nanohole sensor with a gas sample or a condensed phased sample; and (iii) optically analyzing the gas or condensed phase sample at one or more (such as 2, 5, 10, 20, 25, 50, 75, 100, or more) temperatures (e.g., using a varied temperature program).

In one embodiment, the analysis is performed using step-wise increases and/or decreases of temperature.

In one embodiment, the analysis is performed at one or more temperatures between about room temperature and about 45° C. or about room temperature and about 35° C., such as between about 25° C. and about 45° C., or between about 25° C. and about 35° C.

In one embodiment, the analysis is performed by measuring the intensity change at the peak wavelength of the sensor when exposed to gas/condensed phase analytes.

In another embodiment, the analysis is performed by measuring the intensity change at multiple wavelengths of the gas/condensed phase sample.

In another embodiment, the analysis is performed by measuring the value change at different color channels, e.g. RGB (red-green-blue) and HSV (hue-saturation-value).

In one embodiment, the analysis is performed using a spectrometer. In another embodiment, the analysis performed using a camera (e.g., a cell phone camera).

In another aspect, the present invention relates to an array comprising a plurality (e.g., two or more) of nanohole array based sensors according to any of the embodiments described herein.

In another aspect, the present invention relates to a condensed/liquid phase tester (e.g., a biosensor, for example for detecting DNA, proteins and/or extracellular vesicles) comprising one or more nanohole array based sensor(s) according to any of the embodiments described herein.

BRIEF DESCRIPTION OF THE FIGURES

FIG. 3 shows the calculated spectral characteristics observed using circular nanoholes with diameters of 250 nm, 300 nm, and 350 nm, and the dependence on the period of the nanoholes.

FIG. 4a shows a simulated electrical field distribution of nanohole arrays of 200 nm and 50 nm diameter. FIG. 4b shows how the enhancement varies with nanohole diameter.

DETAILED DESCRIPTION OF THE INVENTION

Definitions

As used herein, the term "nanohole-based" refers to a nanostructured material which has been patterned and processed to have repeated indentations (such as circular indentations) across the surface of a material.

As used herein, the term metal organic framework (MOF) refers to a compound comprising one or more metal ions or clusters coordinated to one or more organic ligands to form a one-, two-, or three-dimensional structure.

LSPR sensors are typically based upon ordered, nanostructured arrays. Nanohole arrays represent one approach to effect LSPR enhancement for sensor applications. LSPR involves oscillation at a certain wavelength for incident light. When the local environment changes, such as when gas molecules are adsorbed on the surface of the nanoholes, the oscillating wavelength shifts.

Figure 1:
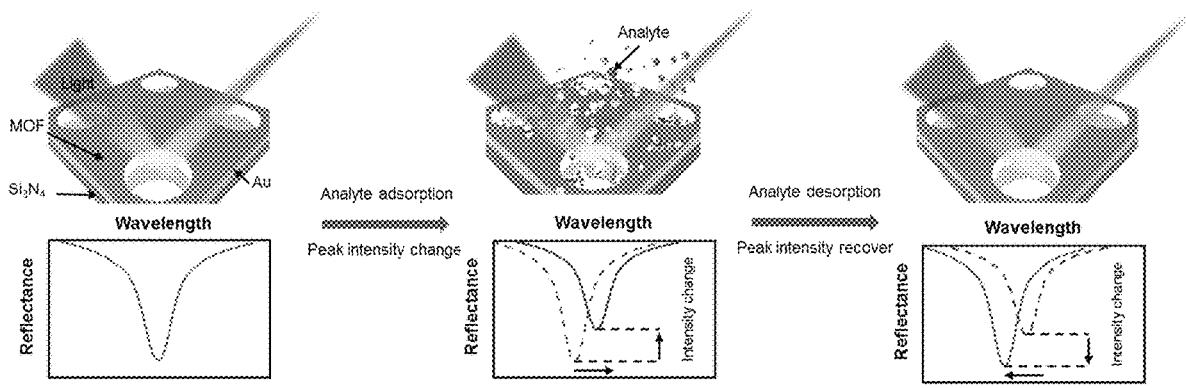
FIG. 1 depicts an exemplary schematic of the sensing principle for the nanohole array based sensors described herein.

FIG. 1 shows a non-limiting schematic of the sensing principle involved in the arrays described herein. As can be seen from FIG. 1, broadband light interacts with the MOF-coated NHA sensor and a reflectance peak can be observed due to LSPR. When the sensor is exposed to, for example, gas analytes, the reflectance spectrum shifts because of the change of the local environment near the nanoholes as the analyte molecules are adsorbed by the MOF. The spectrum shifts back when gas analytes desorb from the MOF coated on the sensor.

Optimization of the Nanohole Sensor Based Arrays
Optimization of the Size, Shape and Period of the Nanoholes For the measurements described herein, peak intensity changes resulting from adsorption of analytes are reported, since this monitoring approach exhibits less noise than measuring the shift in peak position itself. With the lower noise, the limit of detection may be lowered and the transient responses are more repeatable and more readily measured. However, to generate signals that are most sensitive and useful, it is helpful to use simulation of the field behavior to pre-determine which surface feature sizes, shapes and periods provide optimal spectral characteristics (see, e.g., FIGS. 2, 4 and 16). This input guides the device fabrication process.

Figure 2:
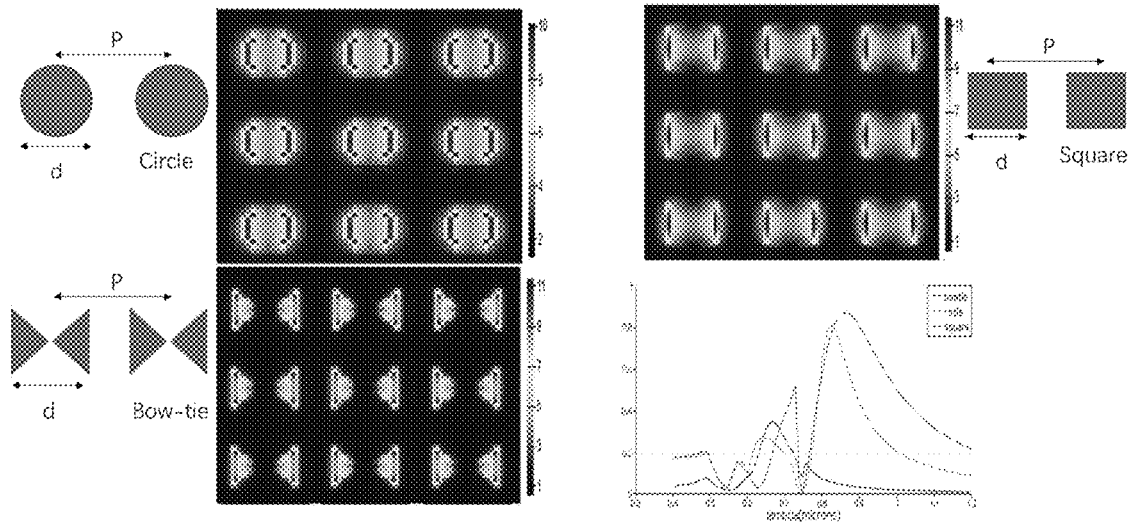
FIG. 2 shows results modelling the electrical field distribution and spectral characteristics of different nanohole shapes (circles, square, and bowties).

FIG. 2 shows the electrical field distribution and spectral characteristics of different nanohole shapes (circles, square, and bowties). The size (300 nm), period (500 nm), and material (gold) remained constant.

As can be seen from FIG. 2, the selected polarization (in the 'z' direction) results in the strongest electrical field being located at the edges of the holes. The bowtie shaped nanoholes exhibit the highest electrical field, which leads to the sharpest peak wavelength. Sharp peaks typically provide higher sensitivity since even small shifts can be easily measured. The peak wavelength of the bowtie shaped nanoholes appears at about 650 nm, while the peak wavelength of circle and square shaped nanoholes appears at about 800 nm. However, due to their smaller transmission area, the intensity from the bowtie shaped nanoholes is actually about half that observed for the circle and square shaped nanoholes.

The effect of the size of the nanohole was also studied. FIG. 3 (left) shows the effect on the spectral profile observed using circular nanoholes with diameters of 250 nm, 300 nm, and 350 nm, respectively. The period (500 nm), and material (gold) remained constant. Since the periods are the same, the peak wavelength does not change (around 800 nm). As the size decreases, the intensity drops slightly while the sharpness increases. FIG. 3 (right) shows the effect of the spectral profile observed at different periods (500 nm, 550 nm, and 600 nm). The size was calibrated as half of the period in each group to keep the shape of waveform unchanged.

FIG. 4a shows the simulated electrical field distribution of the NHA of 200 nm and 50 nm respectively. It is estimated from the simulation that the 50 nm diameter nanoholes provide maximum enhancement in the electric field as compared to the holes with higher dimensions (see FIG. 4b). For example, a 50 nm diameter nanohole array exhibits about 4.5 times the electric field enhancement than a 200 nm diameter nanohole array. It is shown that the electrical field enhancement increases as the dimensions of the nanohole array decreases. During the simulation, the period of the nanohole array is kept at 2 times the diameter of the nanohole (P=2d).

Figure 16:
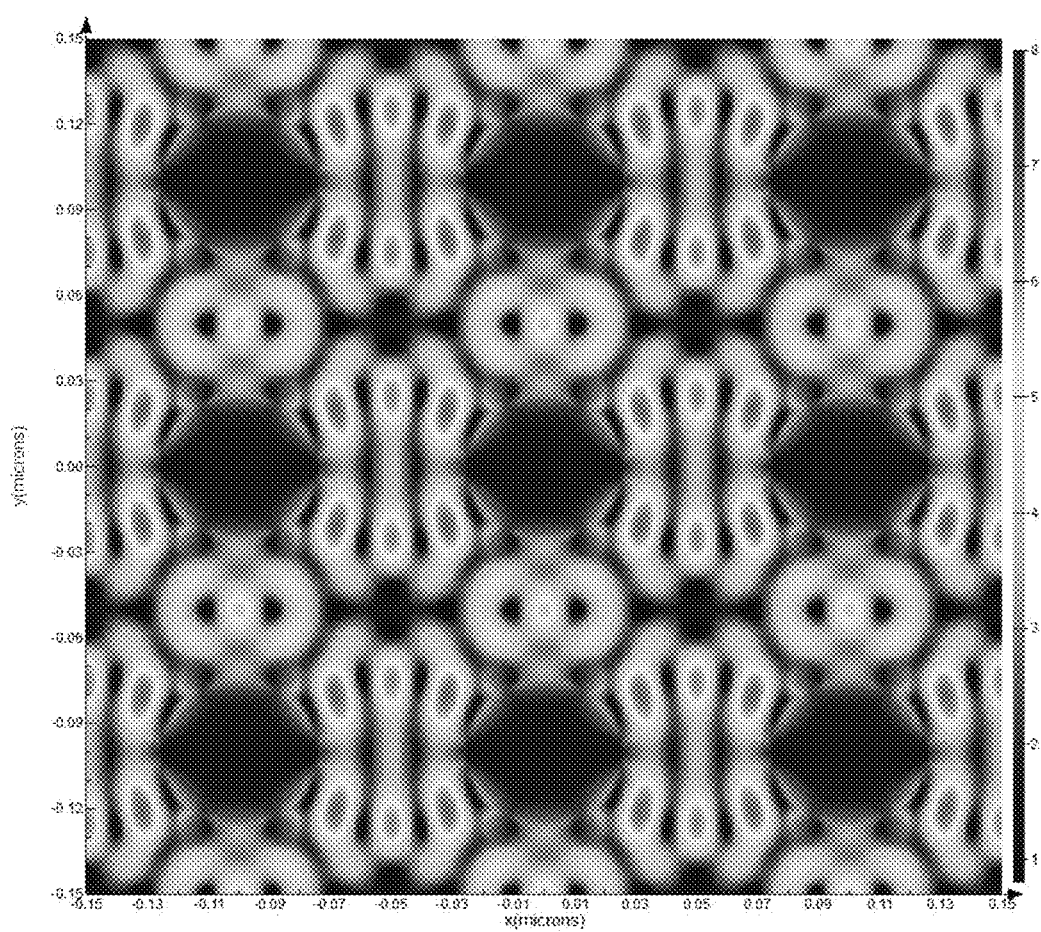
FIG. 16 shows a simulated E-field enhancement of nanohole arrays (r=50 nm) surrounded by nanoparticles (10 nm).

It is estimated that adding nanoparticles around the NHA patterns can further improve the enhancement of the electric field. FIG. 16 shows a simulated E-field enhancement of nanohole arrays (r=50 nm) surrounded by nanoparticles (10 nm). The E-field is increased more over than 100% when nanoparticles are decorated close to the edges of the nanoholes.

Fabrication Process

Figure 5:
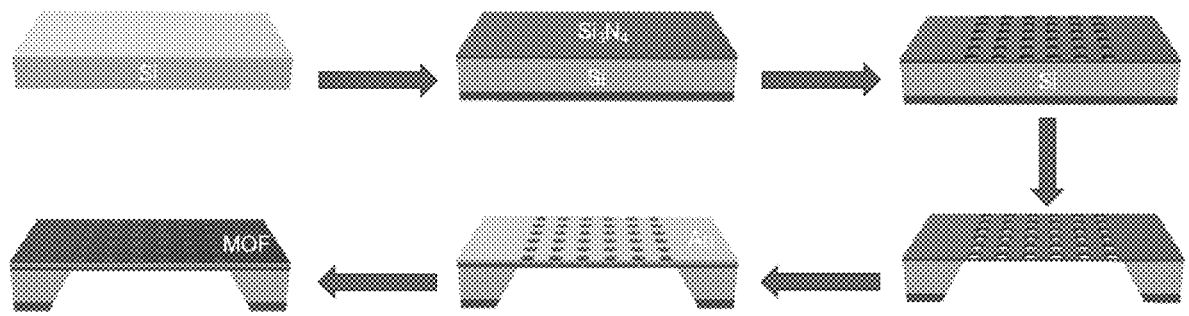
FIG. 5 depicts an exemplary fabrication process for preparing a nanohole array based sensor, from the initial substrate through to the top surface functional coating.

FIG. 5 depicts an exemplary fabrication process for preparing nanohole based arrays according to the present invention. In one embodiment, the exemplary process involves:

(i) depositing 100 nm thick $Si_3N_4$ on a Si substrate using e.g., low-pressure chemical vapor deposition (LPCVD);

(ii) patterning the nanohole array using e.g., a deep UV stepper or E-beam lithography and reactive ion etching (RIE);

(iii) optionally patterning a Pt heater surrounding the NHA pattern area using, e.g., a mask aligner and E-beam evaporator.

(iv) patterning the membrane window on the backside of $Si_3N_4$ layer using, e.g., a mask aligner and RIE etching, then etching the Si to create the membrane by etching, using, e.g., potassium hydroxide;

(v) depositing an adhesion layer of 5 nm titanium and a layer of 80 nm gold on top of the sample, using e.g., an E-beam evaporator;

(vi) coating the product of step (iv) with one or more layers of a metal organic framework (e.g., Cu-BTC).

Using this exemplary process, over 100 nanosensor chips may be made each time on a 100 mm wafer. The design of and process steps used to add the heater are compatible with portions of the device added before or after the heater. Furthermore, the design and operation of the heater are compatible with operation of the sensor as a plasmonic device.

FIG. 6 depicts schematic, photographic, and micrographic images of an exemplary fabricated sensor. Scanning electron microscope (SEM) images of uncoated and metal organic framework coated nanohole arrays are included. As shown in FIG. 6a, circular nanoholes are patterned on a thin $Si_3N_4$+Au membrane. The sensor is coated with one or more layers of Cu-BTC metal organic framework for better sensing performance. In essence, the sensor 100 has a substrate 102, deposited film of $Si_3N_4$ layer 104, 106, a plasmonic (gold) layer 108, and a functional coating 110 (e.g., MOF, capture affinity layer). The substrate 102 forms one or more legs of the sensor 100 that support the plasmonic (e.g., gold) layer 108 and the functional (e.g., MOF) layer 110. A gap or space 101 is formed between the legs of the substrate 102 that permits a gas to be detected to flow unobstructed between the legs. The substrate 102 can be silicon and has top and bottom surfaces.

Figure 6A:
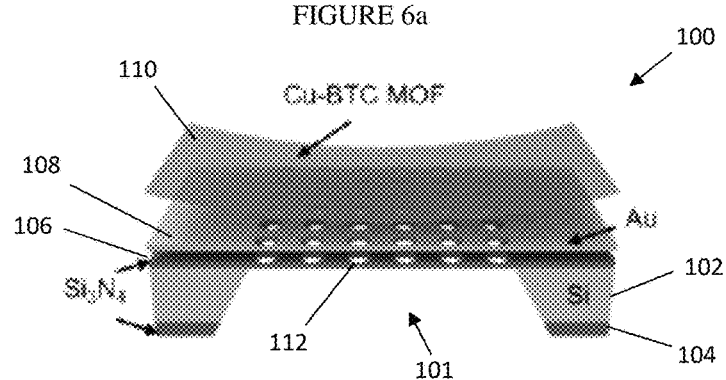
FIGS. 6a-6f depict schematic (FIG. 6a), photographic (FIG. 6b), and micrographic images (FIGS. 6c-6f) of an exemplary fabricated nanohole array based sensor.

The bottom surface of the substrate 102 can be coated with a deposit, such as $Si_3N_4$. The $Si_3N_4$ deposited layer 106 is on the top surface of the substrate 102 and forms a thin planar layer 106 that spans a space 101 between the substrate legs 102. The plasmonic (e.g., gold) layer 108 is planar and on top of the $Si_3N_4$ deposited layer 106 and in one embodiment can cover the entire $Si_3N_4$ deposited layer 106. The functional (e.g., MOF) layer 110 is on top of the plasmonic (e.g., gold) layer 108 and in one embodiment can cover the entire plasmonic (e.g., gold) layer 108. The functional (e.g., MOF) layer has better adsorption of gases to be detected by the sensor 100, thereby increasing the performance of the sensor 100 (e.g., increasing the sensitivity, limit of detection). The plasmonic (e.g., gold) layer 108 does not significantly adsorb gases Accordingly, the functional (e.g., MOF) layer 110, plasmonic (e.g., gold) layer 108, and $Si_3N_4$ deposited layer 106 each span a space formed by the substrate 102. One or more through-holes or openings 112 extend through each of those layers 106, 108, 110. The one or more through-holes or openings 112 may be formed on the deposit layer 106 by a fabrication process, and layers 108 and 110 are may be added thereafter. The openings 112 can be arranged in any suitable configuration, such as in rows and columns, as shown in FIG. 6a. The holes 112 are positioned in the space 101 between the substrate 102 so that a gas to be detected (as well as light from the light source) can pass unobstructed through the openings 112. The gas is thus adsorbed by the MOF layer 110 to locate analyte proximal to the enhancing region of the nanohole edges where signal (peak shift resulting in changed intensity) is generated. The sensor 100 is shown as being substantially square or rectangular in shape, but any suitable size and shape can be provided. And the holes 112 need not be circular, but can be any suitable size and shape depending on the gas/condensed phase to be sensed. In one embodiment, the holes 112 can have a diameter of between e.g., about 200 nm and about 350 nm, or between about 50 nm and about 200 nm.

Figure 6B:
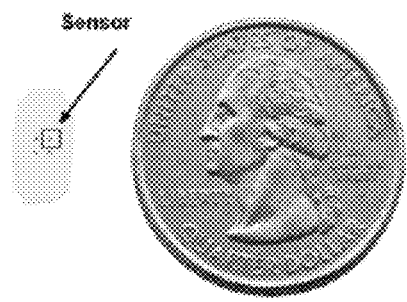
Figure 6C:
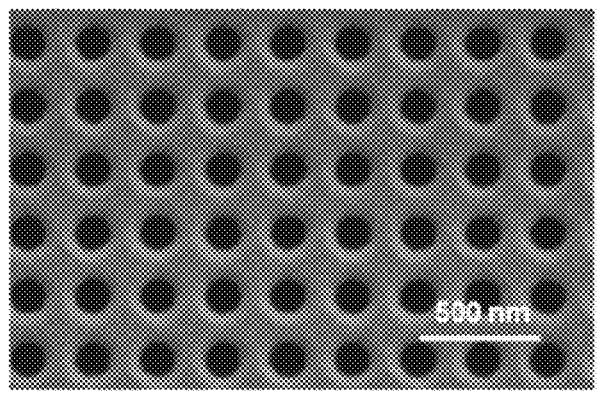
Figure 6D:
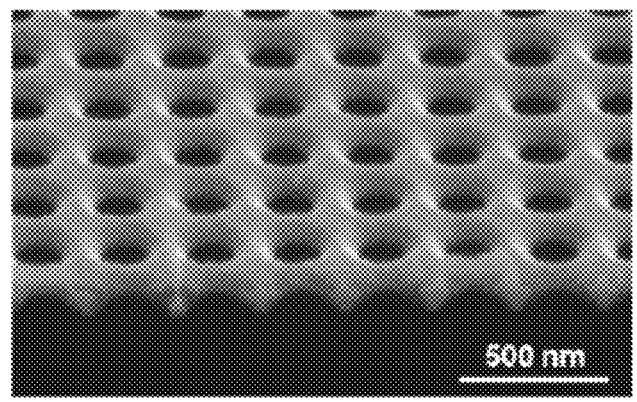
Figure 6E:
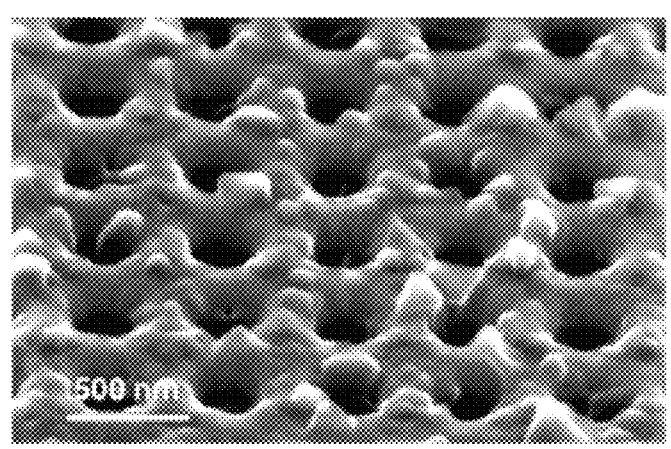
Figure 6F:
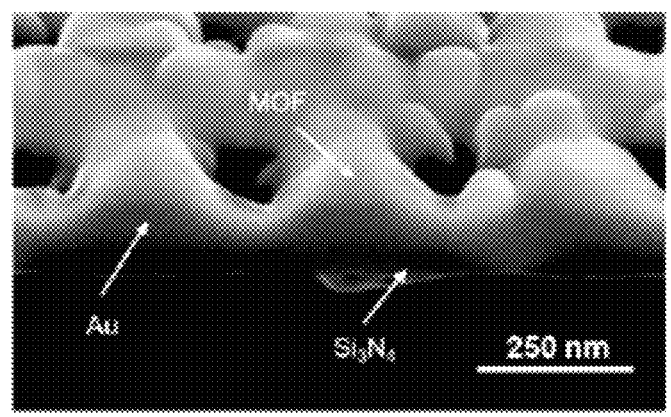

FIG. 6b shows the image of one sensor chip. Each chip contains, e.g., 4 nanohole array windows each with an area of 300 μm×300 μm. FIGS. 6c and 6d show SEM images of the uncoated nanohole array structure. The nanoholes 112 have a 200-nm diameter and a 400-nm period. The membrane contains a layer 106 of 100 nm thickness $Si_3N_4$ and a layer 108 of 80 nm thickness Au. FIGS. 6e and 6f show SEM images of the metal organic framework coated nanohole array structure. As can be seen, the SEM image shows that the coating of metal organic framework is distributed both on the top surface as well as the sidewalls of the nanoholes, which is particularly beneficial for the sensing platform, as the most enhanced LSPR occurs at the edges of the nanoholes, which corresponds to the MOF-decorated hole edges where analyte molecules are expected to be adsorbed into the MOF. The hole diameter of the coated nanohole array was reduced to 170 nm, which indicates that the thickness of the metal organic framework 110 is approximately 15 nm (i.e., approximately 1 nm per layer).

Optimization of the Functional (e.g., Metal Organic Framework) Layer

Nanohole array sensors coated with different thicknesses of Cu-BTC MOF were tested (5, 10, 15 or 20 layers) to determine the optimized thickness for gas sampling. For the analytes studied, the maximum sensor response was found for 15-layers of MOF coating.

Figure 7A:
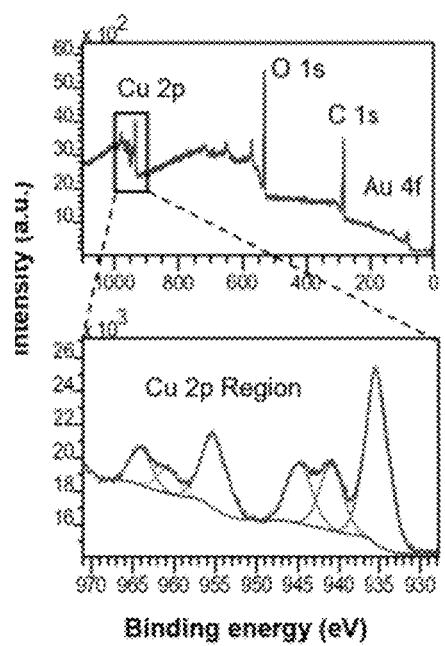
FIG. 7a shows the XPS spectra for nanohole array based sensors coated with 5, 10, 15 and 20 layers of Cu-BTC MOF.
Figure 7B:
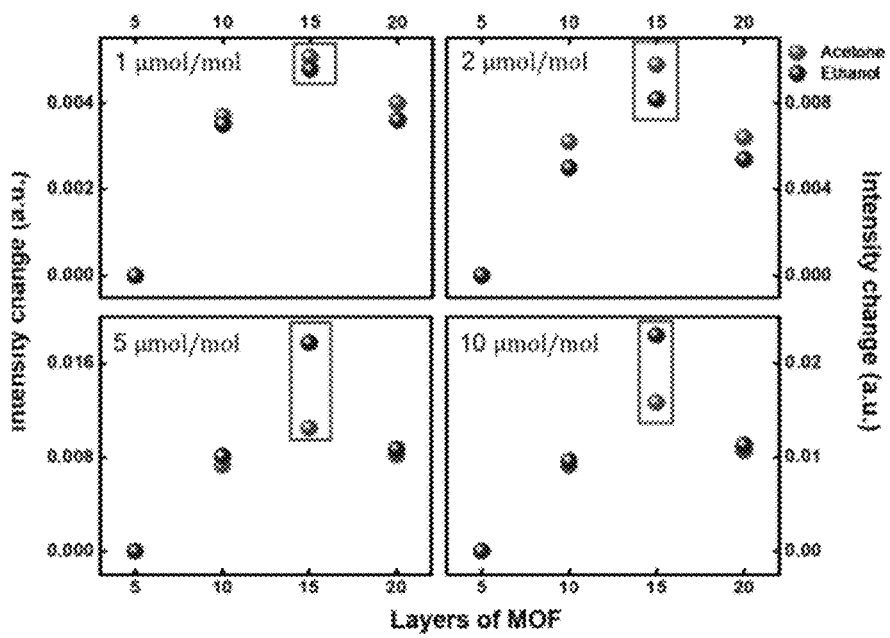
FIG. 7b shows signals measured when sensors with different MOF thickness are exposed to acetone and ethanol vapors at concentrations of 1, 2, 5 and 10 μmol/mol in air.

FIG. 7a shows X-ray photoelectron spectroscopy (XPS) spectra of the coated samples, confirming the presence of the Cu-BTC MOF. FIG. 7b shows signal intensity for samples coated with 5, 10, 15 and 20 layers of Cu-BTC MOF exposed to acetone and ethanol vapors at 1, 2, 5 and 10 μmol/mol.

Measurement of Gas Sample Concentration

Figure 8A:
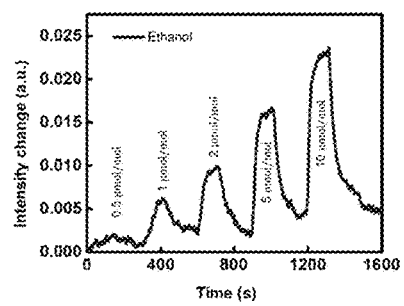
FIGS. 8a-8c show the relative changes of intensity with time when the nanohole array based sensor is exposed to the different concentrations of acetone and ethanol.
Figure 8B:
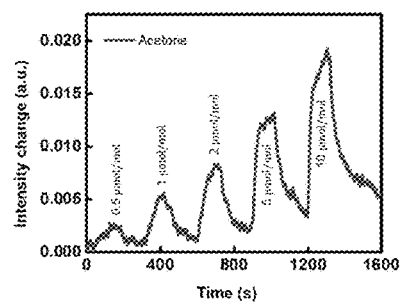

FIGS. 8a and 8b show the relative changes of intensity with time when the sensing element is exposed to the different concentrations of acetone and ethanol vapors in air at room temperature. As can be seen, the sensors described herein can detect approximately 500 nmol/mol of ethanol or acetone at room temperature. The time for the sensor to reach its maximum is less than 1 min for concentrations approximately 2 μmol/mol. For lower concentrations, the time can be longer to reach the maximum.

Figure 8C:
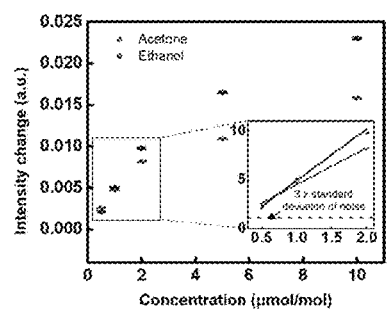

FIG. 8c shows an inflection point in the signal change vs. concentration plot. From the linear dependence of the sensor responses at concentrations approximately 2 μmol/mol, the limit of detection at three-fold of the noise levels can be estimated to be approximately 100 nmol/mol.

Despite the similarity in chemical structure and molecular mass for the two analytes (acetone and ethanol), it is notable that differences are observed in sensor response parameters, particularly for the sensitivity and limits of detection.

Optimization of Nanohole Based Array Temperature—Based Target Discrimination

When sensing an analyte with unknown concentration, it is difficult to determine the analyte's identity and concentration only with the response at room temperature because the information in the response is not sufficient to find two unknowns, i.e. the identity and concentration of an analyte. See e.g., Zhao et al., "Miniaturized nano-hole array based plasmonic sensor for the detection of acetone and ethanol at room temperature and insights into the kinetics of adsorption and plasmonic sensing," DOI 10.1039/xxxxxxxxxx.

A useful approach to enable greater discrimination is to obtain sensing responses at different temperatures to inform on the identity of a molecule and its concentration. The interaction of acetone and ethanol with the MOF-coated sensor are reflected in the change of optical intensity at a fixed wavelength and how the temperature-dependent interactions affect the intensity changes.

Kinetic analysis can help one understand temperature-dependent response behavior.

For example, assuming that interaction of gas (G) with the MOF sensor structure (S) produces the adduct SG which leads to the change of optical intensity (Equation 1).

$$G + S \rightarrow SG \tag{1}$$

The forward rate constant of the above equation is defined as $k_a$. Considering that the number of active sites on the sensor structure is conserved, one can write Equation 2:

$$S(\theta) + SG \rightarrow F_\theta \text{(total available sites)} \tag{2}$$

It is assumed that Fe is a function of the sensor structure and temperature and that for a fixed temperature the number of total sites remains constant. The formation of SG determines the response kinetics of the sensor. As the amount of SG increases, the change in the intensity value increases. Therefore, the response of the sensor is directly proportional to the concentration of SG. The rate of sensor response can be described by the Equation 3:

$$d[SG]/dt = k_a[S]C \tag{3}$$

where C represents the concentration of gas.

Rewriting Equation (3) in terms of respective site occupancies provides Equation 4:

$$d[SG]/dt = ka[F_\theta - SG][G] \tag{4}$$

where [G]~C. Solving Equation 4 provides:

$$[SG](t) = F_\theta(1 - \exp k^a Ct) \tag{5}$$

The maximum response corresponds to the situation when all the active sites ($F_\theta$) are occupied by the reaction product (SG).

Therefore, the response transient can be expressed by the Equation 6:

$$S(t) = S_{max}(1 - \exp k^a Ct) \tag{6}$$

Equation 6 can also be written as Equation 7:

$$S(t) = S_{max}(1 - e^{(-t/\tau)}) \tag{7}$$

where $\tau = 1/k_a C$ is referred to as the characteristic response time for sensing of gases.

Figure 9A:
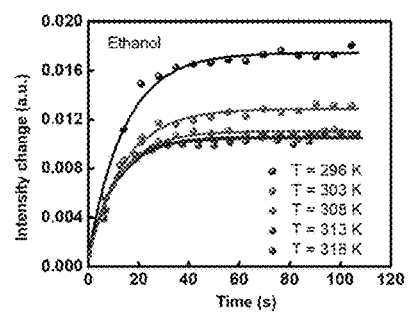
FIGS. 9a-9c show the modeled time-dependent response of the MOF nanohole array based sensors (based on Equation 7) for exposure in an air background to 5 μmol/mol ethanol and the 5 μmol/mol acetone.
Figure 9B:
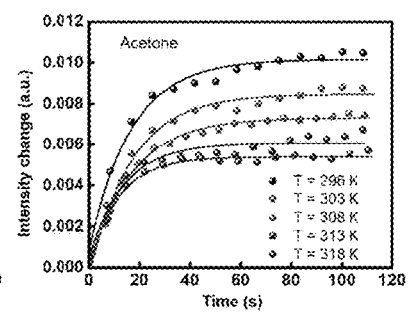

FIG. 9 shows the modeled time-dependent response of the MOF sensor based on Equation 7 for exposure to 5 μmol/mol ethanol (FIG. 9a) and the same concentration of acetone (FIG. 9b), sensing in the operating temperature range 296 K to 318 K. From fitting of the multiple temperature response data, the value of respective characteristic time constants can be estimated.

Table 1 summarizes the estimated time constants values for the detection of acetone and ethanol gases at each of the individual operating temperatures (95% confidence interval).

TABLE 1

| Gas | $\tau_{296}$ (s) | $\tau_{303}$ (s) | $\tau_{308}$ (s) | $\tau_{313}$ (s) | $\tau_{318}$ (s) |
|---|---|---|---|---|---|
| Acetone | 20 ± 3 | 18 ± 2 | 17 ± 2 | 14 ± 2 | 12 ± 2 |
| Ethanol | 14 ± 2 | 14 ± 2 | 12 ± 2 | 11 ± 1 | 11 ± 1 |

The characteristic time constants estimated from the model decrease with increasing operating temperature. The activation energies for the adsorption of acetone and ethanol are estimated from the temperature dependence of the characteristic time constants (t) as shown in Equation 8.

$$t = t_0 \exp(E_A/kT) \tag{8}$$

where $E_A$ is the activation energy for the adsorption of gas on MOF structure, k is the Boltzmann constant, and T is the absolute temperature.

Figure 9C:
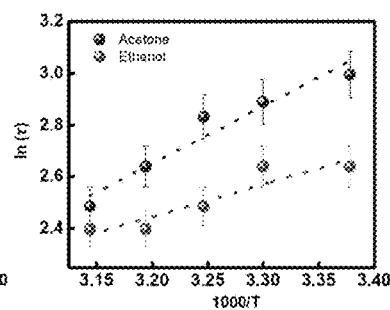

FIG. 9c shows the plots of 1 n τ as a function of 1000/T, which provide the values of activation energies for adsorption.

The estimated activation energies for the interaction of 5 μmol/mol acetone and ethanol are 0.188±0.025 eV and 0.107±0.014 eV respectively. As estimated, the activation energy for interaction of gases over the MOF is higher for acetone than ethanol. For example, since the activation energy for the interaction of the studied analytes (i.e., acetone and ethanol) over the developed sensing material is different, one can understand why kinetic behavior can assist in the discrimination of the different gas types. Thus, it can be beneficial for the sensors described herein to be operated with a dynamically varied temperature, i.e., a temperature programmed method of operation (e.g., using an integrated microheater) and the transient stage of the sensor responses at each tested temperature can be measured.

In one embodiment, a temperature programmed method of operation including step-wise increases and/or decreases of temperature at varying rates, which may provide a signal stream with enriched analytical information. See, e.g., Rogers et al., "Development of optimization procedures for application-specific chemical sensing." *Sensors and Actuators B: Chemical*, 163.1, 8-19, 2012.

EXPERIMENTAL

The present invention is now further illustrated by means of the following non-limiting disclosure.

Preparation of Nanohole Based Array Sensors

FIG. 5 schematically shows an exemplary fabrication process for the NHA sensors described herein. The fabrication process may differ when a micro-heater is embedded or the sensor is used for liquid/condensed phase sensing.

The exemplary represented process for preparation of a gas sensor includes: (i) depositing 100 nm thick $Si_3N_4$ on a Si substrate with low-pressure chemical vapor deposition (LPCVD), (ii) patterning 200 nm circular hole arrays with a deep UV stepper/E-beam lithography and RIE etching, (iii) patterning the membrane window on the backside of $Si_3N_4$ layer with mask aligner and RIE etching, (iv) etching Si to create the membrane by KOH etching, and (v) depositing 5 nm Ti+80 nm Au on top of the sample with an E-beam evaporator. With this method, over 100 nanosensor chips can be made each time on a 100 mm wafer. Each chip contains 4 sensing areas (FIG. 6b).

An exemplary fabrication process for a sensor with a micro-heater includes: (i) depositing 100 nm thick $Si_3N_4$ on a Si substrate with low-pressure chemical vapor deposition (LPCVD), (ii) patterning 200 nm circular hole arrays with a deep UV stepper/E-beam lithography and RIE etching, (iii) depositing an insulating layer on the substrate while keeping the sensor area uncovered with a mask aligner and E-beam evaporator (iv) patterning the Pt micro-heater surrounding the sensor area with a mask aligner and E-beam evaporator, (v) patterning the membrane window on the backside of $Si_3N_4$ layer with mask aligner and RIE etching, (vi) etching Si to create the membrane by KOH etching, and (vii) depositing 5 nm Ti+80 nm Au on top of the sample with an E-beam evaporator.

An exemplary fabrication process for a liquid/condensed phase sensor with a micro-heater includes: (i) depositing 100 nm thick $Si_3N_4$ on a Si substrate with low-pressure chemical vapor deposition (LPCVD), (ii) patterning 200 nm circular hole arrays with a deep UV stepper/E-beam lithography and RIE etching, (iii) depositing an insulating layer on the substrate while keeping the sensor area uncovered with a mask aligner and E-beam evaporator (iv) patterning the Pt micro-heater surrounding the sensor area with a mask aligner and E-beam evaporator, and (v) depositing 5 nm Ti+80 nm Au on top of the sample with an E-beam evaporator.

The exemplary Cu-BTC MOF used in the studies described herein was coated layer-by-layer to generate the thin layer of MOF. Each 4-sensor chip was first submerged in a self-assembling-monolayer (SAM) solution (100 μmol/L 4-mercaptobenzoic acid/ethanolic solution) 37 for 1 hour. The method described in Zhao et al., *J. Mat. Chem. A*, 3, 1458-1464, 2015 was adapted to coat thin layers of MOF on the sample. 1,3,5-benzenetricarboxylic acid (BTC, 98% v/v, Acros Organics) and copper (II) acetate monohydrate (99% v/v, Sigma Aldrich) were dissolved separately in two vessels with ethanol to make 1 mmol/L solutions. During the coating process for each layer, the SAM-coated sensor chip was first dipped in BTC solution for 5 minutes and rinsed in ethanol for 1 minute. The chip was then transferred to the copper (II) acetate monohydrate solution for 5 minutes and then rinsed in ethanol for 1 minute. During each transfer between solutions, the chip was dried in air for 10 seconds. The coating process was repeated multiple times to afford the Cu-BTC MOFs with varied thicknesses. To avoid breaking the suspended platforms, a shaker (IKA KS 130 control with IKA AS 130.1 attachment) was used instead of a sonicator during the coating process. The shaking rate was set to 100/minute.

System Setup and Sensor Characterization

Figure 10:
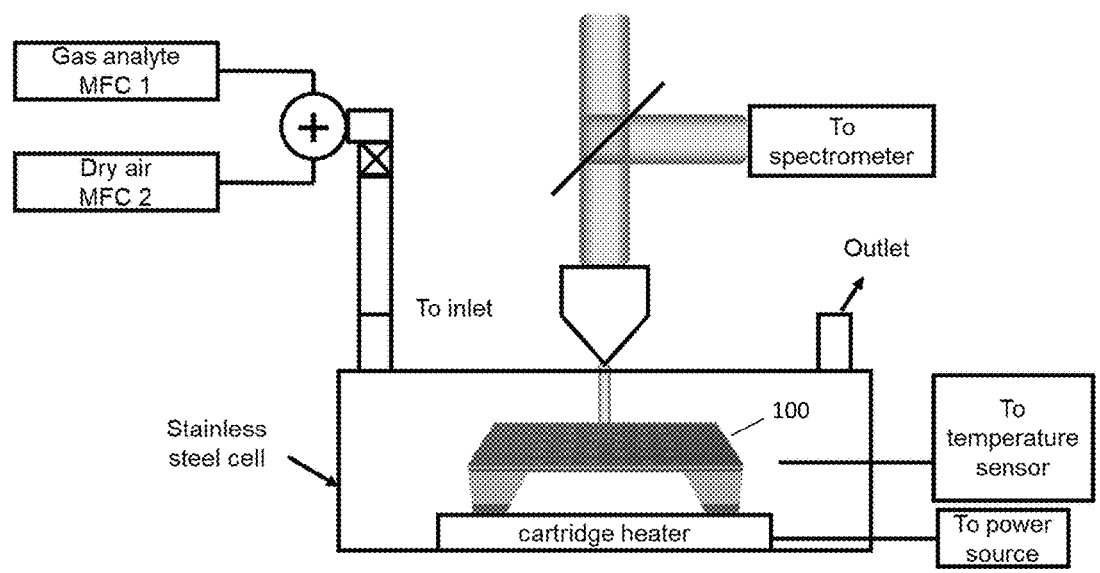
FIG. 10 shows an exemplary reflection-based optical setup used for the measurements described herein.

FIG. 10 shows an exemplary reflection-based optical setup used for the analysis described herein. A broadband visible light source (400 nm-700 nm) is focused on the sensor 100 by a microscope. The reflected signal from one of the four sensing areas is deflected by a mirror to be captured by a spectrometer (Thorlabs CCS 17538). As a means of initial demonstration of the temperature-varied operation (prior to fabricating our optical sensing platform with an integrated microheater) a cartridge heater (OMEGA CSH-10110038) can be inserted in the housing for the sensor 100 to control the sensor temperature. The housing can be, for example, a closed box or stainless-steel cell that encloses the sensor 100 and has an interior space in which a gas can flow and be controlled. In this exemplary embodiment, the sensor 100 can be positioned on top of the heater. The housing can have openings to receive the microscope, gas inlet, and gas outlet. Target gases (e.g. acetone and ethanol) from cylinders are mixed with dry air to generate different concentrations. Mass flow controllers (MFCs) (MKS38) are used to control the concentration and flow rate of the gases into the housing through an inlet (which can be controlled by a one-way valve), through the openings of the sensor 100, and out through the outlet (which can be controlled by a one-way valve). The total flow rate was controlled at 2 standard L/min (slm) for each test. In other embodiments, the flow rate may range between about 0.1 and about 2 slm or between about 0.005 and about 5 slm. An airtight housing is provided to illustrate one embodiment of the invention in which the sensor is contained in a confined space. However, the housing need not be airtight and need not be provided, and the sensor 100 can be positioned at any suitable location where a gas is to be sensed.

Use of an Integrated Heater

Figure 11:
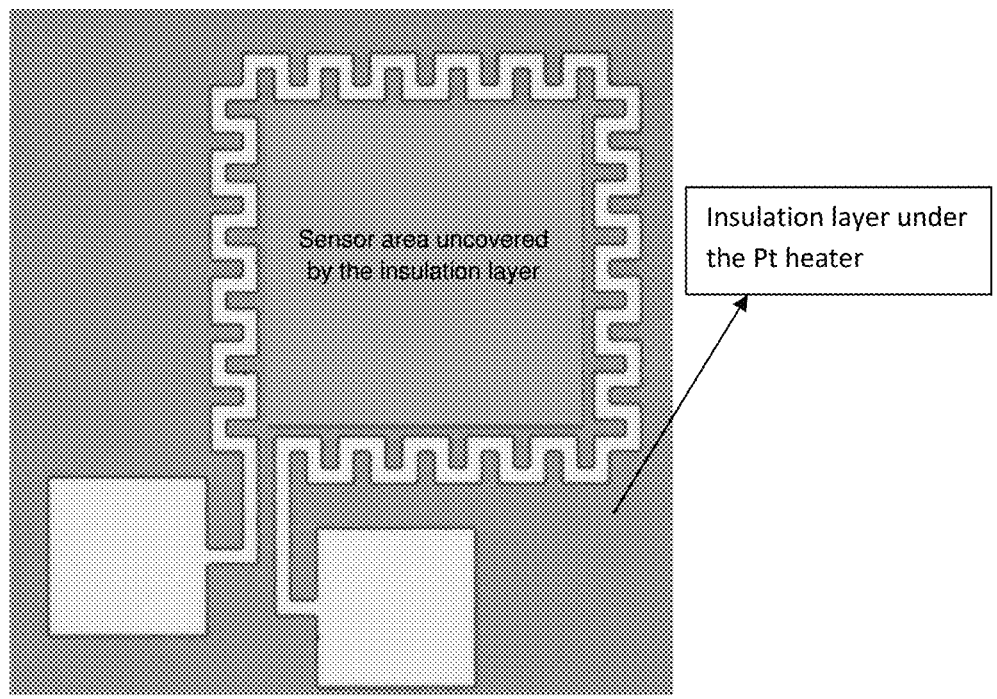
FIG. 11 depicts an exemplary micrograph of a fabricated Pt microheater surrounding the NHA structure in a nanohole array based sensor. An insulation layer is added below the Pt heater while leaving the central area (sensor area) uncovered by the insulation layer.

In another embodiment, an integrated heater is added to supplement and/or substitute for the cartridge heater and maintains the planar structure of the sensor. For example, a 200-nm thick Pt heater 120 may be placed around the NHA pattern to provide temperature control of the sensing platforms and avoid blocking the light transmit through the NHAs. An exemplary micrograph of a fabricated Pt microheater is shown in FIG. 11. Temperature changes produced by the heater can be directly measured by the heater resistance (as it can act as a platinum resistance thermometer (PRT)).

Figure 12A:
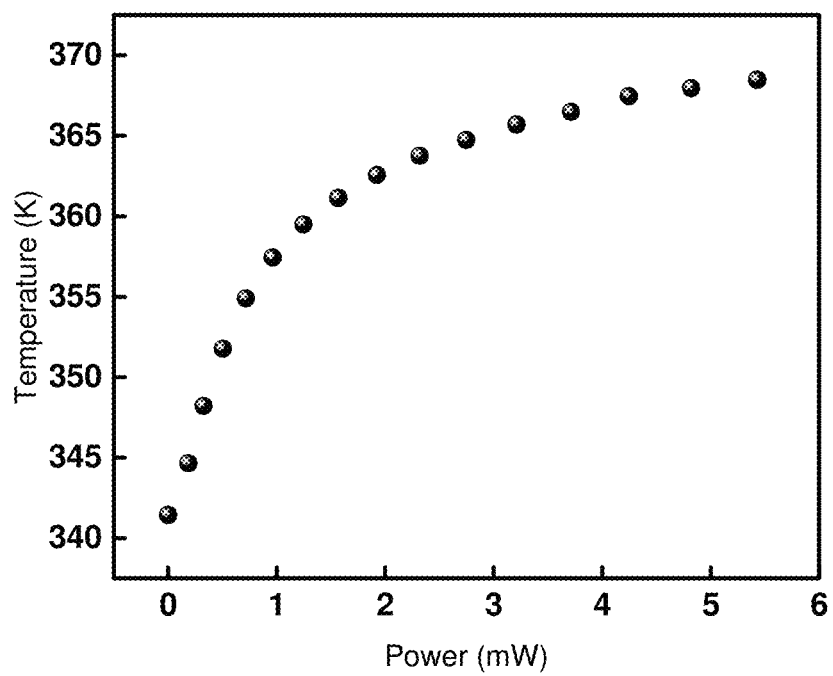
FIG. 12a shows the power consumption of an embedded micro-heater versus surface temperature, which is a testing result on a micro-heater without a thin membrane. The surface temperature can be much higher when a thin membrane is etched from below the micro-heater at the same power consumption.
Figure 12B:
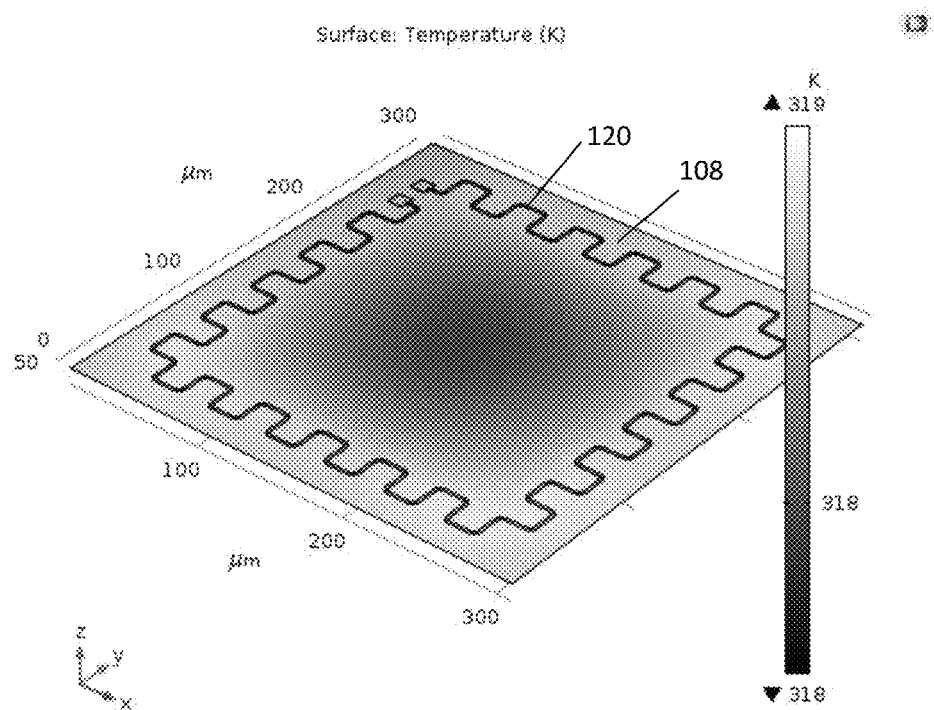
FIG. 12b shows simulated temperature gradient results of the embedded microheater.

FIG. 12a shows the power consumption of the microheater versus surface temperature. The microheater consumes power in mW, over 1000 times lower than a cartridge heater. FIG. 12b shows simulation result of the microheater. As can be seen from FIG. 12b, the temperature gradient of the area is less than 1 K, showing that the heat is uniformly distributed.

As shown in FIG. 12b, the heater 120 can be placed on the top surface of one of the planar layers, here shown as the planar top surface of the gold layer 108. However, an insulator layer (such as $Si_3N_4$ or $SiO_2$) is placed between the gold layer 108 and the Pt heater 120 so that the heater doesn't short. The gold layer is a plasmon source, and also generates a hot-plate effect to uniformly distribute heat in the NHA area. The MOF is coated as the last step, so that the heater 120 doesn't sit on top of the MOF layer.

The heater 120 extends around the holes 112 in the form of an unclosed square shape having two ends that are separated by a slight gap so that the heater 120 doesn't short circuit when a current is applied. The heater 120 can extend close to the edges of the gold layer 108 (FIG. 11b), or at one section of the gold layer 108 (FIG. 12b). The heater 120 extends substantially about all of the holes 112 so that the holes 112 are enclosed by the heater 120. As further illustrated, the heater 120 can have any suitable shape to further facilitate even distribution of the heat, such as for example a square wave shape, or a serpentine shape with parallel or anti-parallel segments, which further mitigate the potential effects of the magnetic fields caused by the operating microheater. The MOF layer 110 is then placed over top of the heater 120 and gold layer 108, which bonds to the gold layer 108, but doesn't bond to the heater 120, which can be made of Pt. Temperature from the heater can be directly measured by the heater resistance (as it can act as a platinum resistance thermometer (PRT)).

The heater 120 can be a metal lead line, wire, or thin plate. A voltage differential can be applied at the two ends via lead lines to generate a current that flows through the heater 120 to create heat that heats the gold layer 108, as well as the MOF layer 110 and the $Si_3N_4$ layer 106.

The heater 120 is generally placed outside of the holes 112 to minimize any electrical disturbance that the metal may otherwise cause. The heater 120 is configured to create an even temperature distribution throughout the sensor layers 106, 108, 110 and achieve a desired temperature that maximizes the sensitivity of the MOF layer 110 with respect to the specific gas being detected. The leads can also be used to sense or detect the temperature of the heater 120 and the MOF layer 110. It should be noted that the heater 120 can have other suitable shapes and configurations. For example, the heater 120 can be a circular ring or one or more linear strips placed along the sides of the gold layer 108. The heater 120 can also extend between the holes of the nanohole array, though that could cause unwanted electrical disturbances.

The existence of the micro-hotplate may allow one to vary the local temperatures during the sensing periods. The sensing performance of NHA sensors may be measured at "m" different operating temperatures, where "m" is the number of temperatures applied during the sensing period.

Figure 13:
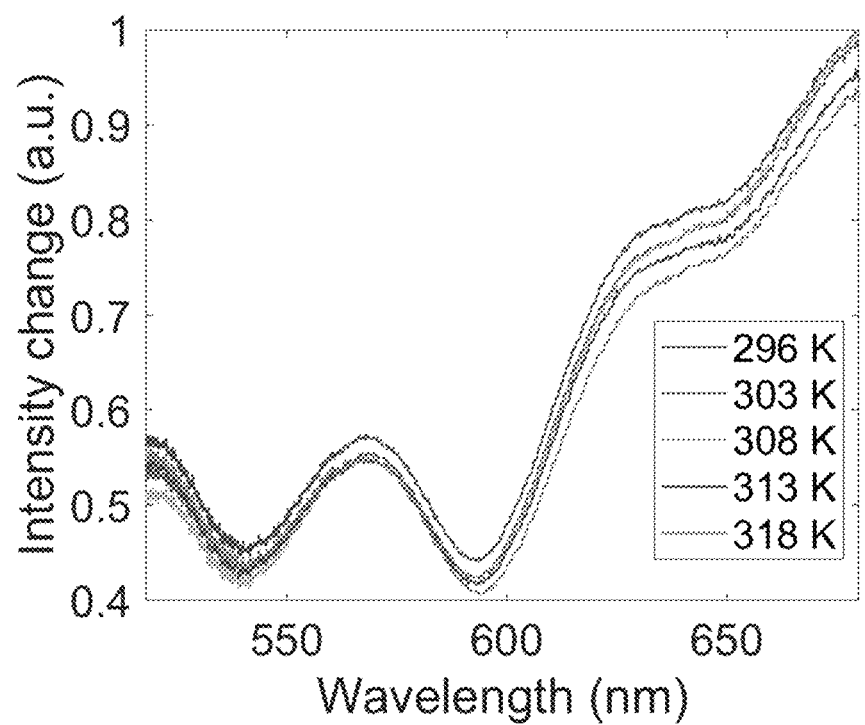
FIG. 13 shows the spectra of the MOF-coated nanohole array based sensors at different temperatures from 296 K to 318 K.

FIG. 13 shows the spectra of the MOF-coated sensor when exposed under dry air. The intensity changes at the resonance peak are measured during the gas sensing process. The spectrum is measured in a reflection-based configuration and therefore the resonance peak is inverted (occur as a valley) at different temperatures were measured and shown in FIG. 13. The spectra red shift as the temperature increases because the refractive index of the material (mainly from Au and Si) increases as temperature increases from 296 K to 318 K. The information can be used to calibrate the baseline of the sensor during the measurements.

Measurement at Multiple Wavelengths

Figure 14:
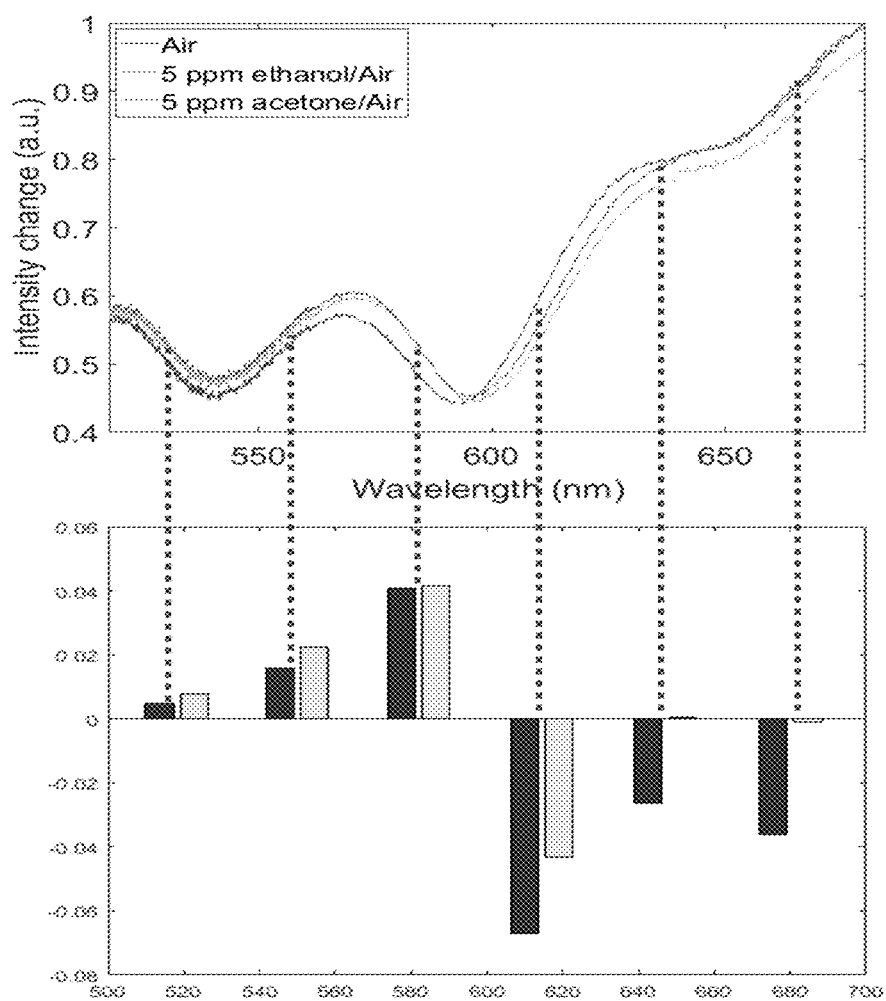
FIG. 14 shows an example of a multi-wavelength measurement for 5 mol/mol ethanol/air and 5 mol/mol acetone/air.

Measurement of the intensity change at multiple wavelengths instead of only at a single peak position may help to improve the selectivity of the sensor. An example of a multi-wavelength measurement is shown in FIG. 14. The intensity change difference between acetone and ethanol varies at different wavelengths, Measurement of the intensity change at multiple wavelengths may thereby help to discriminate different gas analytes.

Additional Optical Measurements

In another embodiment, the spectrometer shown in the setup of FIG. 10, is replaced by another optical apparatus, such as a camera (e.g., a cell phone camera), thereby providing a much lower cost alternative to the use of costly spectrometers in such analysis. In the embodiment with a cell phone or other mobile or portable camera, a deflecting lens is not needed and the camera can be positioned to directly image the sensor 100.

Figure 15A:
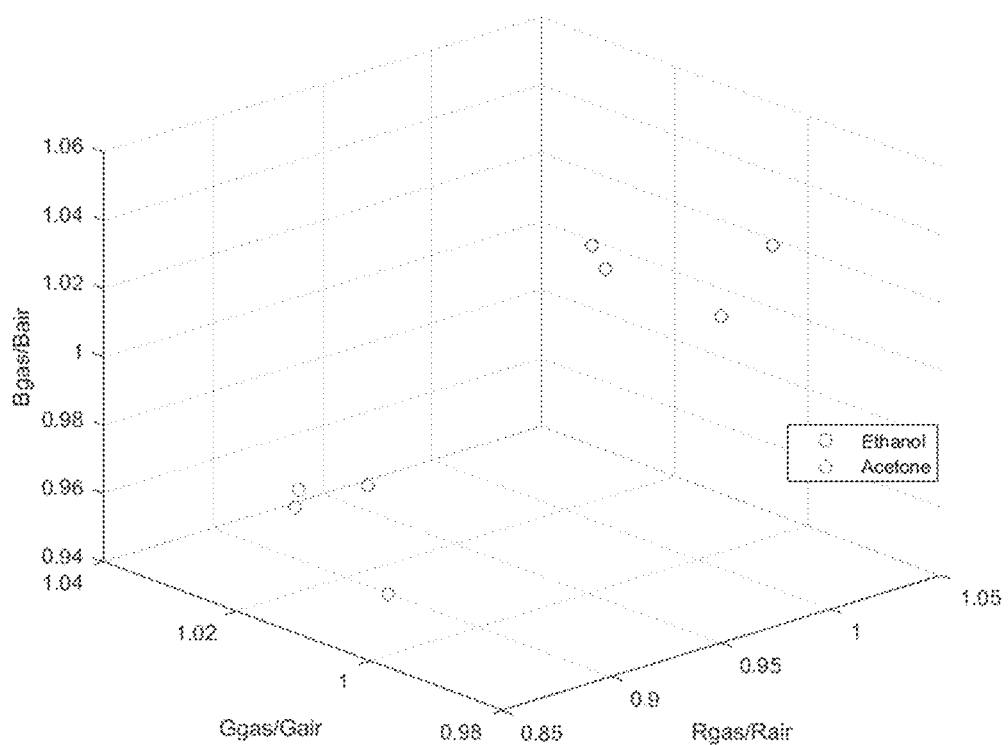
FIG. 15a shows an example of cell-phone camera measurement for gas phase measurement.
Figure 15B:
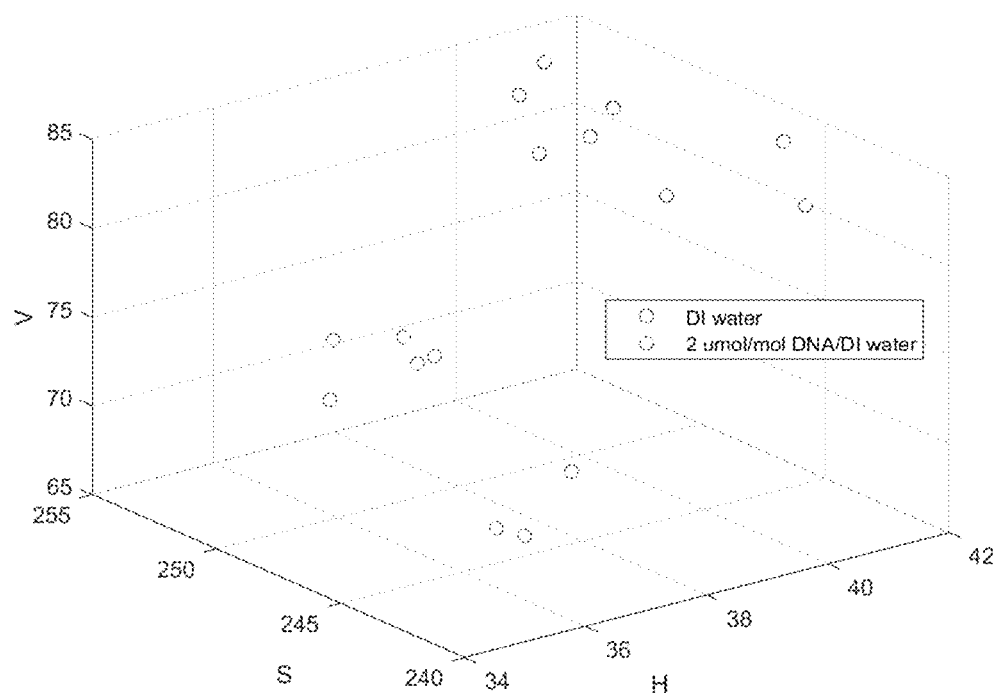
FIG. 15b shows an example of cell-phone camera measurement for DNA measurement (liquid/condensed phase).

FIG. 15a shows an example of processed data measured with a cell-phone camera measurement to discriminate between acetone and ethanol. FIG. 15b shows a condensed phase example demonstrating that DNA binding in the vicinity of the nanohole array can be detected. Other embodiments, where a functional biological coating acts to bind target bio-molecules can offer a way to detect these molecules when the interaction alters the optical environment near the nanoholes. Temperature control using 120 can help in the detection and discrimination of bio-markers. This camera-based approach may help to make portable devices for the sensor arrays. In an experiment, 4 sensor arrays may be measured at the same time, which can help accelerate the process of research and sensor training.

FIG. 16 shows that sensing approaches can further benefit from enhanced E-field generated by the presence of nanoparticles, especially near the edges of the nanoholes.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as described above. It is intended that the appended claims define the scope of the invention and that methods and structures within the scope of these claims and their equivalents be covered thereby.

All publications, patents and patent applications cited in this application are herein incorporated by reference to the same extent as if each individual publication, patent or patent application was specifically and individually indicated to be incorporated herein by reference.

What is claimed is:

1. A nanohole-array based plasmonic sensor comprising:
   i) a substrate at least partially covered with a deposit;
   ii) a plasmonic layer on the deposit; and
   iii) one or more functional layers on the plasmonic layer;
   wherein the sensor comprises a plurality of nanoholes, and
   wherein the one or more functional layers have a thickness of between about 5 nm and about 20 nm.

2. The sensor according to claim 1, wherein the substrate is an etchable substrate.

3. The sensor according to claim 1, wherein the substrate is silicon.

4. The sensor according to claim 1, wherein the substrate is covered with a deposit selected from $Si_3N_4$, $SiO_2$, and a combination thereof.

5. The sensor according to claim 1, wherein the deposit is $Si_3N_4$.

6. The sensor according to claim 1, wherein the deposit has a thickness of between about 20 nm and about 600 nm.

7. The sensor according to claim 1, wherein the plasmonic layer comprises gold, silver, copper, aluminum, platinum, or any combination thereof.

8. The sensor according to claim 1, wherein the plasmonic layer comprises gold.

9. The sensor according to claim 1, wherein the plasmonic layer has a thickness of between about 5 nm and about 300 nm.

10. The sensor according to claim 1, wherein the one or more functional layers comprise a metal organic framework, DNA, a protein, an aptamer, or any combination thereof.

11. The sensor according to claim 1, wherein the sensor comprises between 1 and about 20 layers of the functional layer.

12. The sensor according to claim 1, wherein the sensor comprises about 15 layers of the functional layer.

13. The sensor according to claim 1, wherein the functional layer comprises a biological layer that interacts with one or more target bio-molecules.

14. The sensor according to claim 13, wherein the one or more biomolecules comprise DNA, a protein, an aptamer, or any combination thereof.

15. The sensor according to claim 1, wherein the functional layer comprises copper 1,3,5 benzenetricarboxylate.

16. The sensor according to claim 1, wherein the sensor comprises circular nanoholes.

17. The sensor according to claim 1, wherein the nanoholes have a diameter ranging between about 10 and about 500 nm, between about 50 and about 350 nm, between about 100 and about 350 nm, between about 150 and about 350 nm, or between about 200 and about 350 nm.

18. The sensor according to claim 1, wherein the nanoholes have a diameter of about 25 nm, about 50 nm, about 75 nm, about 100 nm, about 125 nm, about 150 nm, about 175 nm, about 200 nm, about 225 nm, about 250 nm, about 275 nm, about 300 nm, about 325 nm, or about 350 nm.

19. The sensor according to claim 1, wherein the period of the nanoholes is between about 50 nm and about 1000 nm, between about 300 nm and about 600 nm or between about 400 nm and about 500 nm.

20. The sensor according to claim 1, wherein the plasmonic nanohole arrays are further coated with nanoparticles.

21. The sensor according to claim 1, wherein the sensor further comprises an integrated heater.

22. A method of making a sensor comprising:
   (i) depositing a covering on a substrate;
   (ii) patterning a nanohole array on the covered substrate;
   (iii) depositing an insulation layer on the covered substrate while leaving the nanohole array area uncovered
   (iv) patterning a heater on the covered substrate;
   (v) patterning a membrane window on the backside of the covered substrate;

(vi) etching the substrate to create a membrane,
(vii) depositing a plasmonic layer on top of the substrate, wherein the plasmonic layer is deposited at the central area with respect to the heater; and
(viii) coating the plasmonic layer with one or more functional layers, wherein the one or more functional layers have a thickness of between about 5 nm and about 20 nm.

23. A method of detecting/analyzing one or more gases present in a gas sample or analyzing a condensed/liquid phase sample, the method comprising:
   (i) providing a nanohole sensor according to claim 1;
   (ii) contacting the nanohole sensor with a gas sample or a condensed/liquid phase sample; and
   (iii) optically analyzing the gas or condensed/liquid phase sample at one or more temperatures.

24. The method of claim 23, wherein the analysis is performed under step-wise changes in temperature.

25. The method of claim 23, wherein the analysis is performed by measuring the intensity change at the peak wavelength of the gas sample.

26. The method of claim 23, wherein the analysis is performed by measuring the intensity change at multiple wavelengths of the gas sample.

27. The method of claim 23, wherein the analysis is performed by measuring the value change in color channels of the sensor exposed to the gas sample or condensed liquid phase sample.

28. An array comprising a plurality of sensors according to claim 1.

29. A condensed/liquid phase sensor comprising a sensor according to claim 1.

30. The sensor according to claim 1, wherein the one or more functional layers comprise a metal organic framework.

31. The sensor according to claim 1, wherein the sensor is adapted for detecting/analyzing one or more gases present in a gas sample and/or analyzing a condensed/liquid phase sample.

32. The method according to claim 22, wherein the sensor is adapted for detecting/analyzing one or more gases present in a gas sample and/or analyzing a condensed/liquid phase sample.

33. The method according to claim 23, wherein the analysis is performed using a spectrometer.

34. The method according to claim 23, wherein the analysis is performed using a camera.

35. The nanohole-array based plasmonic sensor according to claim 1, wherein the sensor is a gas-phase sensor.

36. The nanohole-array based plasmonic sensor according to claim 1, wherein the sensor is a condensed/liquid phase sensor.

37. The nanohole-array based plasmonic sensor according to claim 1, wherein the one or more functional layers have a thickness of between about 10 nm and about 20 nm.

38. The nanohole-array based plasmonic sensor according to claim 1, wherein the one or more functional layers have a thickness of about 15 nm.

39. A nanohole-array based plasmonic gas-phase sensor comprising:
   i) a substrate at least partially covered with a deposit;
   ii) a plasmonic layer on the deposit; and
   iii) one or more functional layers on the plasmonic layer;
   wherein the sensor comprises a plurality of nanoholes,
   wherein the one or more functional layers comprise a metal organic framework (MOF); and
   wherein the one or more functional layers have a thickness of between about 5 nm and about 20 nm.

40. The nanohole-array based plasmonic gas-phase sensor according to claim 39, wherein the plasmonic layer has a thickness between about 50 and about 100 nm.

41. The nanohole-array based plasmonic gas-phase sensor according to claim 39, wherein the plasmonic layer has a thickness of about 80 nm.

42. The nanohole-array based plasmonic gas-phase sensor according to claim 39, wherein the nanoholes have a diameter of about 200 nm.

43. The nanohole-array based plasmonic sensor according to claim 39, wherein the one or more functional layers have a thickness of between about 10 nm and about 20 nm.

44. The nanohole-array based plasmonic sensor according to claim 39, wherein the one or more functional layers have a thickness of about 15 nm.

* * * * *